(12) United States Patent
Wilson

(10) Patent No.: US 8,538,033 B2
(45) Date of Patent: Sep. 17, 2013

(54) SYSTEMS AND METHODS FOR OBTAINING HEARING ENHANCEMENT FITTINGS FOR A HEARING AID DEVICE

(75) Inventor: Gerald A. Wilson, South Jordan, UT (US)

(73) Assignee: Sonic Innovations, Inc., Salt Lake City, UT (US)

( * ) Notice: Subject to any disclaimer, the term of this patent is extended or adjusted under 35 U.S.C. 154(b) by 642 days.

(21) Appl. No.: 12/551,985

(22) Filed: Sep. 1, 2009

(65) Prior Publication Data

US 2011/0051942 A1    Mar. 3, 2011

(51) Int. Cl.
*H04R 29/00* (2006.01)

(52) U.S. Cl.
USPC ............ 381/60; 381/23.1; 381/320; 381/321; 381/72

(58) Field of Classification Search
USPC ............... 381/312, 316, 320, 321, 23.1, 303, 381/305, 60, 72, 314, 315, 323, 329; 700/94; 600/559; 73/585; 379/52; 703/2
See application file for complete search history.

(56) References Cited

U.S. PATENT DOCUMENTS

| | | | |
|---|---|---|---|
| 5,202,927 A | 4/1993 | Topholm | |
| 5,226,086 A | 7/1993 | Platt | |
| 5,604,812 A | 2/1997 | Meyer | |
| 5,838,801 A | 11/1998 | Ishige et al. | |
| 6,004,015 A | 12/1999 | Watanabe et al. | |
| 6,035,050 A | 3/2000 | Weinfurtner et al. | |
| 6,044,163 A | 3/2000 | Weinfurtner | |
| 6,148,274 A | 11/2000 | Watanabe et al. | |
| 6,522,988 B1 | 2/2003 | Hou | |
| 6,741,712 B2 | 5/2004 | Bisgaard | |
| 6,748,089 B1 | 6/2004 | Harris et al. | |
| 6,876,751 B1 | 4/2005 | Gao et al. | |
| 6,985,598 B1 | 1/2006 | Joschika | |
| 7,024,000 B1 | 4/2006 | Gabara et al. | |
| 7,068,793 B2 | 6/2006 | Shim | |
| 7,200,237 B2 | 4/2007 | Zhang et al. | |
| 7,295,121 B2 | 11/2007 | Aceti | |
| 7,515,720 B2 | 4/2009 | Schwob | |
| 7,564,979 B2 | 7/2009 | Swartz | |
| 2001/0033664 A1 | 10/2001 | Poux et al. | |
| 2003/0133578 A1* | 7/2003 | Durant | 381/60 |
| 2005/0129262 A1 | 6/2005 | Dillon et al. | |
| 2005/0192515 A1* | 9/2005 | Givens et al. | 600/559 |
| 2006/0171550 A1 | 8/2006 | Bryant et al. | |
| 2007/0003077 A1 | 1/2007 | Pedersen et al. | |
| 2007/0019818 A1 | 1/2007 | Kurz | |
| 2007/0195979 A1 | 8/2007 | Thomasson et al. | |

(Continued)

FOREIGN PATENT DOCUMENTS

DE        10038118 A1    2/2002
EP        0695107 A1     1/1996

(Continued)

*Primary Examiner* — Vivian Chin
*Assistant Examiner* — Leshui Zhang
(74) *Attorney, Agent, or Firm* — Birch, Stewart, Kolasch & Birch, LLP

(57) ABSTRACT

A computer-implemented method for obtaining hearing enhancement fittings for a hearing aid device is described. A plurality of audiograms is collected. The plurality of audiograms is divided into one or more sets of audiograms. A representative audiogram is created for each set of audiograms. A hearing enhancement fitting is computed from each representative audiogram. A hearing aid device is programmed with one or more hearing enhancement fittings computed from each representative audiogram.

20 Claims, 7 Drawing Sheets

(56) References Cited

U.S. PATENT DOCUMENTS

| | | |
|---|---|---|
| 2007/0223721 A1 | 9/2007 | Stern et al. |
| 2007/0230726 A1 | 10/2007 | Giesner et al. |
| 2007/0237346 A1 | 10/2007 | Fichtl et al. |
| 2008/0025538 A1 | 1/2008 | Zad-Issa |
| 2008/0040116 A1 | 2/2008 | Cronin et al. |
| 2008/0041656 A1 | 2/2008 | Burrows et al. |
| 2008/0044034 A1 | 2/2008 | Hou |
| 2008/0049956 A1 | 2/2008 | Hou |
| 2008/0056518 A1 | 3/2008 | Burrows et al. |
| 2008/0107294 A1 | 5/2008 | Burrows et al. |
| 2008/0125672 A1 | 5/2008 | Burrows et al. |
| 2008/0165980 A1 | 7/2008 | Pavlovic et al. |
| 2008/0187145 A1 | 8/2008 | Burrows et al. |
| 2008/0212789 A1 | 9/2008 | Cronin et al. |
| 2008/0221719 A1* | 9/2008 | Margolis et al. ............... 700/94 |
| 2008/0226105 A1 | 9/2008 | Barthel et al. |
| 2008/0240452 A1 | 10/2008 | Burrows et al. |
| 2008/0253579 A1 | 10/2008 | Cronin et al. |
| 2008/0267435 A1 | 10/2008 | Schumaier |
| 2008/0269636 A1 | 10/2008 | Burrows et al. |
| 2008/0298600 A1 | 12/2008 | Poe et al. |
| 2008/0298614 A1 | 12/2008 | Cronin et al. |
| 2009/0060214 A1 | 3/2009 | Wessel et al. |

FOREIGN PATENT DOCUMENTS

| | | |
|---|---|---|
| EP | 1363473 A2 | 5/2003 |
| EP | 1601232 A2 | 11/2005 |
| EP | 1727395 A2 | 11/2006 |
| WO | WO 2005/125280 A2 | 6/2005 |
| WO | WO 2007/052189 A2 | 10/2006 |
| WO | WO 2008/018146 A1 | 2/2008 |
| WO | WO 2008/154706 A1 | 6/2008 |
| WO | WO 2009/001559 A1 | 12/2008 |

* cited by examiner

SYSTEMS AND METHODS FOR OBTAINING HEARING ENHANCEMENT FITTINGS FOR A HEARING AID DEVICE

BACKGROUND

Hearing aid devices are used to enhance or improve the quality of life for the user. These devices may amplify certain sounds that have been unheard to some degree by the user in the past. Because each user of a hearing aid has varying degrees of hearing loss, these devices are programmable for adaptation to the user's needs.

In order to program a hearing aid to be tailored to the user's hearing needs, the user's hearing threshold may be measured using a sound-stimulus-producing device and calibrated headphone. The measurement of the hearing threshold may take place in a sound-isolating room. For example, the measurement may occur in a room where there is very little audible noise. The sound-stimulus-producing device and the calibrated headphones may be referred to as an audiometer.

The audiometer may generate pure tones at various frequencies between 125 Hz and 12,000 Hz that are representative of the frequency bands in which the tones are included. These tones may be transmitted through the headphones of the audiometer to the individual being tested. The intensity or volume of the pure tones is varied until the individual can just barely detect the presence of the tone. For each pure tone, the intensity of the tone at which the individual can just barely detect the presence of the tone is known as the individual's air conduction threshold of hearing. The collection of the thresholds of hearing at each of the various pure tone frequencies is known as an audiogram and may be presented in graphical form.

When the threshold of hearing in each frequency band has been determined, this threshold may be used to estimate the amount of amplification, compression, and/or other adjustment that will be employed in the hearing aid device to compensate for the individual's loss of hearing. As shown by the above, the resources and time required to determine the fitting (i.e., amplification, compression, and/or other adjustments) of a hearing aid for a particular user are extensive. As a result, benefits may be realized by providing improved systems and methods for obtaining hearing enhancement fittings for a hearing aid device.

SUMMARY

According to at least one embodiment, a computer-implemented method for obtaining hearing enhancement fittings for a hearing aid device is described. A plurality of audiograms is collected. The plurality of audiograms is divided into one or more sets of audiograms. A representative audiogram is created for each set of audiograms. A hearing enhancement fitting is computed from each representative audiogram. A hearing aid device is programmed with one or more hearing enhancement fittings computed from each representative audiogram.

In one embodiment, the one or more sets of audiograms may be subdivided into one or more subsets until a termination condition is satisfied. In one configuration, one or more audiograms may be filtered from the plurality of audiograms. For example, one or more audiograms may be filtered from the plurality of audiograms that exceed a specified fitting range for the hearing aid device.

In one embodiment, a mean hearing threshold may be determined at each measured frequency of each audiogram within the plurality of audiograms. Prototype audiograms may be created from the mean hearing threshold. In addition, each prototype audiogram may be associated with a set of audiograms. In one configuration, an audiogram may be placed in the set of audiograms if the audiogram is similar to the prototype audiogram associated with the set. In one embodiment, the creation of a representative audiogram for each set of audiograms may include calculating a mean of each audiogram in a set of audiograms.

A computing device configured to obtain hearing enhancement fittings for a hearing aid device is also described. The computing device may include a processor and memory in electronic communication with the processor. The computing device may also include a collection module configured to collect a plurality of audiograms, and an organization module configured to divide the plurality of audiograms into one or more sets of audiograms. The computing device may further include a representative generation module configured to create a representative audiogram for each set of audiograms. In addition, the computing device may include a fitting generation module configured to compute a hearing enhancement fitting from each representative audiogram and program a hearing aid device with one or more hearing enhancement fittings computed from each representative audiogram.

A computer-program product for obtaining hearing enhancement fittings for a hearing aid device is also described. The computer-program product may include a computer-readable medium having instructions thereon. The instructions may include code programmed to collect a plurality of audiograms, and code programmed to divide the plurality of audiograms into one or more sets of audiograms. The instructions may also include code programmed to create a representative audiogram for each set of audiograms, and code programmed to compute a hearing enhancement fitting from each representative audiogram. In addition, the instructions may include code programmed to program a hearing aid device with one or more hearing enhancement fittings computed from each representative audiogram.

A second computer-implemented method for obtaining hearing enhancement fittings for a hearing aid device is also described. A plurality of audiograms may be collected. A hearing enhancement fitting may be computed from each audiogram of the plurality of audiograms. The hearing enhancement fittings may be divided into one or more sets of fittings. A representative fitting may be created for each set of fittings. A hearing aid device may be programmed with one or more representative hearing enhancement fittings.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
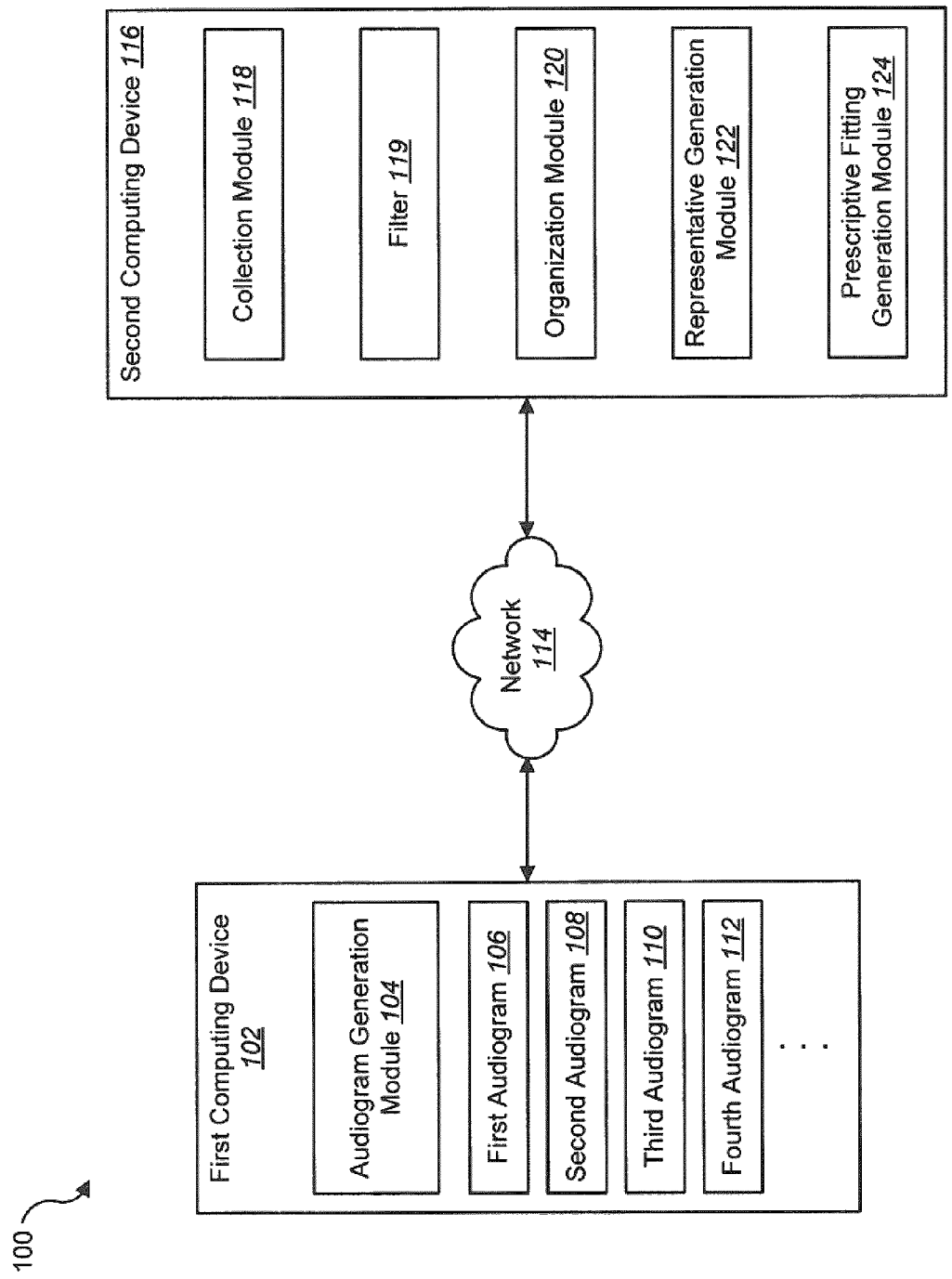
FIG. 1 is a block diagram illustrating one embodiment of a first computing device and a second computing device communicating over a network connection in order to generate prescriptive fitting targets for a hearing aid device.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

Many people have hearing losses that are similar in nature. For example, a high-frequency, sloping hearing loss may be common in age-related hearing loss. Some people may merely find it difficult to differentiate between words that begin with consonantal sounds such as the fricatives or sibilants, z, or th, or the plosives d, t, b, or p. Some may be unable to hear thin, high-pitched or metallic noises.

A hearing aid device may be an electro-acoustic body worn apparatus that typically fits in or behind the wearer's ear. This device may be designed to amplify and modulate sound for the wearer. Dispensers or manufactures of hearing aid devices may program a hearing aid device with a fitting that is specific to the wearer's audiogram. An audiogram may be a graphical representation of the wearer's hearing loss. Once the hearing aid is fitted according to the audiogram, an audiologist and/or the wearer may finely tune or adjust the fitting of the hearing aid until a desired result occurs. Programming each hearing aid based on individual audiograms consumes an enormous amount of time and resources. As previously mentioned, many people have hearing losses that are similar in nature as measured by an audiogram. As a result, the present systems and methods obtain prescriptive fitting targets for hearing aids based on similarities in hearing loss according to multiple audiograms of individuals.

FIG. 1 is a block diagram illustrating one embodiment of a first computing device 102 and a second computing device 116 communicating over a network connection 114 in order to generate prescriptive fitting targets for a hearing aid device. The computing devices 102, 116 may be a personal computer (PC), a laptop, a personal digital assistant (PDA), or any other type of computing device.

In one configuration, the first computing device 102 may be associated with an audiology facility (or other hearing relating testing facility) in order to generate audiograms for individuals. For example, the first computing device 102 may include an audiogram generation module 104 which may gather data from an individual pertaining to the hearing capabilities of that individual. The generation module 104 may then generate an audiogram from the gathered data. In one example, the audiogram generation module 104 may generate a first audiogram 106, a second audiogram 108, a third audiogram 110, and a fourth audiogram 112. While only four audiograms 106, 108, 110, 112 are illustrated, it is to be understood that the audiogram generation module 104 may generate more or less than four audiograms.

In one embodiment, the first computing device 102 may communicate the generated audiograms 106, 108, 110, 112 to a second computing device 116 across the network connection 114. In one example, the second computing device 116 may be associated with a manufacturing facility for hearing aid devices. The second computing device 116 may include a collection module 118 to collect the audiograms 106, 108, 110, 112 received from the first computing device 102. Although FIG. 1 only illustrates a single computing device 102 sending audiograms to the second computing device 116, it is to be understood that the second computing device 116 may receive audiograms from more than one computing device located in different locations than the first computing device 102. For example, multiple computing devices associated with multiple audiologist's offices may generate audiograms for individuals and send these audiograms to the second computing device 116.

In one embodiment, the second computing device 116 may further include a filter 119. The filter 119 may eliminate or exclude one or more audiograms received by the collection module 118. The filter 119 may exclude one or more received audiograms based on certain criteria. For example, hearing aids may be designed for a specific fitting range. The filter 119 may exclude audiograms that exceed the fitting range of a target hearing aid device. The filter 119 may also exclude audiograms based on other factors related to hearing loss or hearing preference such as the age or gender of the individual associated with the audiogram.

In one configuration, the second computing device 116 may also include an organization module 120. The organization module 120 may divide or organize audiograms received by the collection module 118 into one or more sets of audiograms. The organization module 120 may divide the received audiograms into certain sets depending on predetermined criteria. For example, the collected audiograms may be divided into two sets by first determining a mean hearing threshold at each measured frequency across the ensemble of collected audiograms. The computed mean hearing threshold may then be perturbed in some way in order to create two prototypical audiograms. The perturbation may be in a random way or by some heuristic to aid in splitting a set. Each prototype audiogram may be associated with a set. In one configuration, each of the collected audiograms may then be placed into one of two sets based on their relative closeness to one of the two prototype audiograms. In one embodiment, the closeness may be determined by any appropriate distance measure. For example, the mean of the squared differences between the hearing thresholds comprised by a given audiogram and the averaged hearing thresholds comprised by a prototype audiogram over each of the measured frequencies may be used to determine the relative closeness of an audiogram to one of the two prototype audiograms.

In one embodiment, each of the two sets of audiograms may be further subdivided. For example, new mean audiograms may be generated for each of the two sets. The mean audiograms may be perturbed to create new prototype audiograms and the audiograms for each set may be regrouped into smaller subsets based on the relative closeness of a particular audiogram is to a newly generated prototype audiogram. The subsets may be continued to be further subdivided until an appropriate termination condition has been satisfied such as, for example, a desired number of subsets is achieved, a desired minimum error by some error measure is achieved, and the like.

The second computing device 116 may further include a representative generation module 122. The generation module 122 may generate a representative audiogram based on the sets and subsets of audiograms organized by the organization module 120. For example, representative audiograms may be generated by calculating the overall mean of audiograms in a particular subset. A prescriptive fitting generation module 124 may generate one or more prescriptive fittings for a hearing aid based on a representative audiogram created by the representative generation module 122. One or more of the prescriptive fittings may be programmed on a hearing aid device. If more than one fitting is programmed, the wearer of the device may select the prescriptive fitting most appropriate for his/her own hearing loss or comfort. As explained above, the fittings may be obtained from multiple audiograms that may exhibit some degree of similar hearing loss patterns.

In another embodiment, the organization module 120 may not divide the collected audiograms into sets and subsets. In one example, the filter 119 may exclude audiograms that fall outside a particular fitting range of a target hearing aid device. A prescriptive fitting generation module 124 may generate fittings to be programmed on a hearing aid device based on each remaining audiogram. In another example, the filter 119 may not exclude any of the collected audiograms and the generation module 124 may generate fittings based on each audiogram received from the first computing device 102. The generated fittings may be organized into sets and subsets by the organization module 120 in a manner similar to the manner previously described above. Representative fittings may be generated by the representative generation module 122 that are representative of each set or subset of fittings. In one embodiment, one or more of the representative fittings may be programmed into the hearing aid device.

Figure 2:
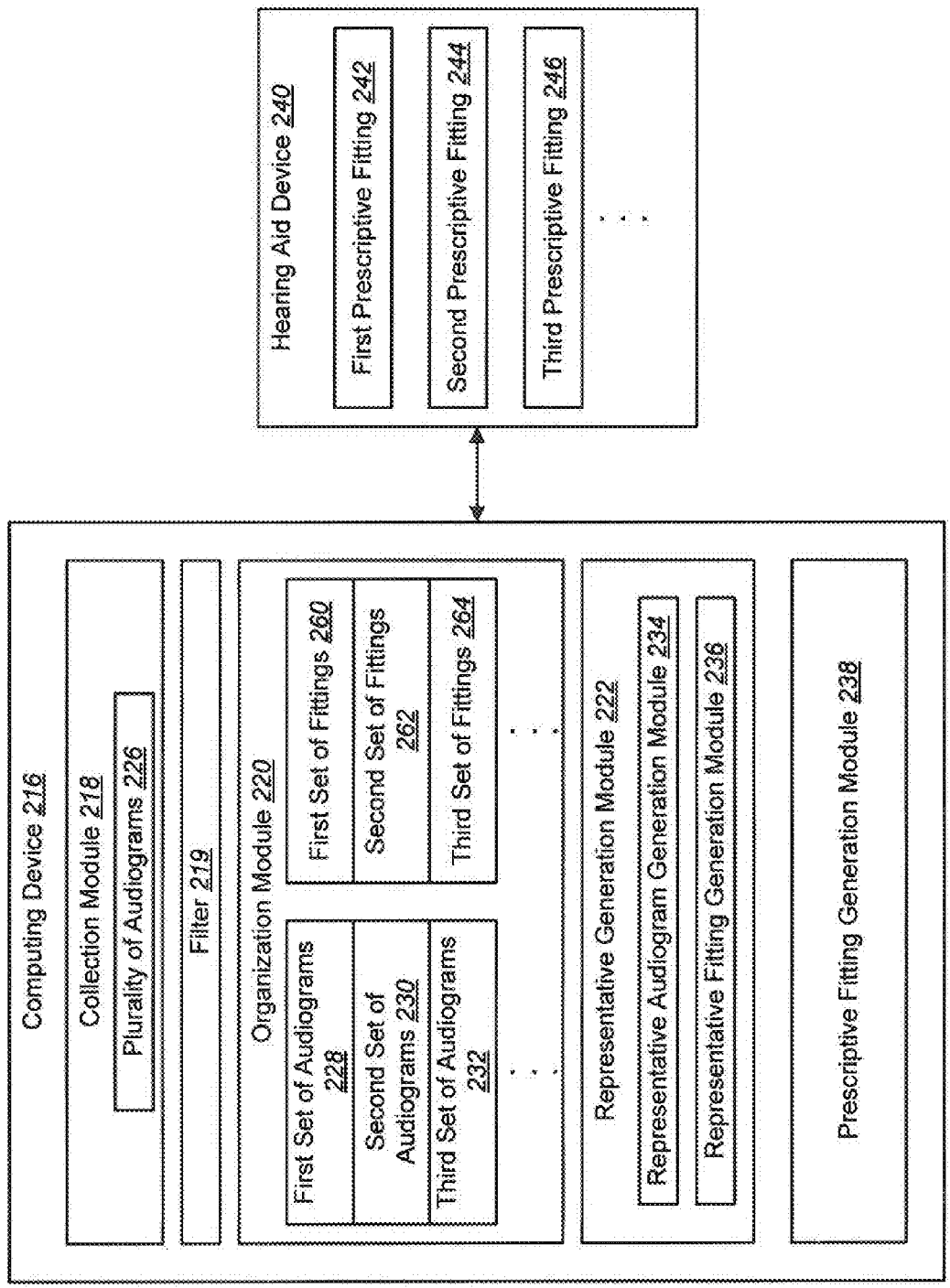
FIG. 2 is a block diagram illustrating a computing device generating prescriptive fittings for a hearing aid device.

FIG. 2 is a block diagram illustrating a computing device 216 to generate prescriptive fittings for a hearing aid device 240. In one configuration, the computing device 216 may include a collection module 218 that collects a plurality of audiograms 226. The plurality of audiograms 226 may be received from one or more computing devices associated with various audiology facilities or other facilities that may test the hearing thresholds of an individual. The computing device 216 may also include a filter 219. The filter 219 may exclude or filter one or more audiograms from the plurality of audiograms 226 based upon a certain criteria. For example, as previously explained, the filter 219 may exclude audiograms that exceed the fitting range of the hearing aid device 240. The computing device 216 may also include an organization module 220. The module 220 may organize or divide each of the audiograms in the plurality of audiograms 226 into one or more sets of audiograms 228, 230, 232. In addition, the organization module 220 may organize or divide prescriptive fittings into one or more sets of fittings 260, 262, 264.

In one configuration, the computing device 216 may further include a representative generation module 222. In one example, the generation module 222 may include a representative audiogram generation module 234. The module 234 may generate one or more representative audiograms from the sets of audiograms 228, 230, 232 created by the organization module 220. In addition, the representative generation module 222 may include a representative fitting generation module 236. The module 236 may generate a representative fitting based on the one or more sets of fittings 260, 262, 264 created by the organization module 220.

Further, the computing device 216 may include a prescriptive fitting generation module 238. The module 238 may generate one or more prescriptive fittings based on the representative audiograms. In one configuration the prescriptive fitting generation module 238 may generate a first prescriptive fitting 242, a second prescriptive fitting 244, and a third prescriptive fitting 246. The generation module 238 may generate more or less than three prescriptive fittings. The generated prescriptive fittings 242, 244, 246 may be programmed into the hearing aid device 240.

In another embodiment, the generation module 238 may generate fittings based on each audiogram within the plurality of audiograms 226. These fittings may then be organized by the organization module 220 into the sets of fittings 260, 262, 264. The representative fitting generation module 236 may generate representative fittings based on the sets of fittings 260, 262, 264. As previously explained, the representative fittings (not shown) may be programmed on the hearing aid device 240.

Figure 3:
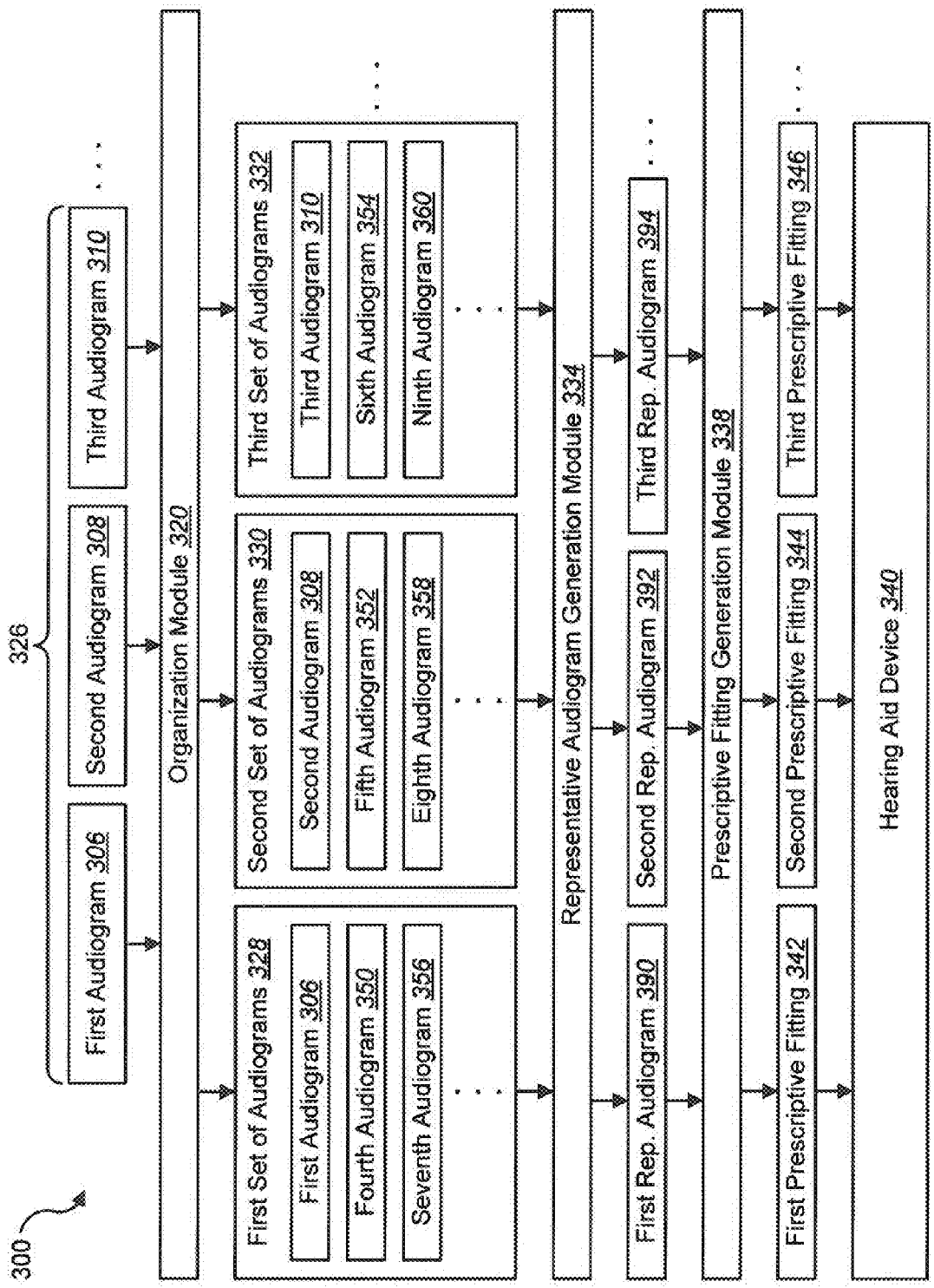
FIG. 3 is a block diagram illustrating one embodiment of various modules used to generate one or more prescriptive fitting targets for a hearing aid device.

FIG. 3 is a block diagram illustrating one embodiment of various modules used to generate one or more prescriptive fitting for a hearing aid device 340. In one configuration, a plurality of audiograms 326 may be provided to an organization module 320. For example, a first audiogram 306, a second audiogram 308, and a third audiogram 310 may be provided to the organization module 320. In one example, there may be more or less than three audiograms that comprise the plurality of audiograms 326.

In one configuration, the organization module 320 may divide or organize the plurality of audiograms 326 into one or more sets of audiograms 328, 330, 332. For example, the organization module 320 may divide some of the audiograms into a first set of audiograms 328. In other words, the first set of audiograms 328 may include the first audiogram 306, a fourth audiogram 350, and a seventh audiogram 356. The first set of audiograms 328 may include more or less than three audiograms. In addition, the organization module 320 may organize or create a second set of audiograms 330 and a third set of audiograms 332. Each of the sets of audiograms may include individual audiograms that are common or similar to each other to a certain degree. For example, each set of audiograms 328, 330, 332 may include individual audiograms that are within a certain degree of error to an average audiogram. The sets of audiograms 328, 330, 332 may be further subdivided into further subsets until a termination condition is satisfied. For clarity and ease of understanding, however, additional subsets of audiograms are not illustrated.

In one embodiment, each of the sets of audiograms 328, 330, 332 may be analyzed by a representative audiogram generation module 334. The generation module 334 may generate a representative audiogram for each set of audiograms. For example, a first representative audiogram 390 may be generated that represents the audiograms 306, 350, 356 within the first set of audiograms 328. Similarly, a second representative audiogram 392 may be generated that represents each audiogram 308, 352, 358 within the second set of audiograms 330. Likewise, a third representative audiogram 394 may be generated that represents the audiograms 310, 354, 360 within the third set of audiograms 332. The representative audiograms 390, 392, 394 may be generated by taking the mean of each set of audiograms 328, 330, 332. For example, the first representative audiogram 390 may be generated by taking the overall mean of the audiograms within the first set of audiograms 328.

In one configuration, each of the representative audiograms 390, 392, 394 may be provided to a prescriptive fitting generation module 338. The generation module 338 may generate a prescriptive fitting 342, 344, 346 from each representative audiogram 390, 392, 394. In other words, a first prescriptive fitting 342 may be generated based on the first representative audiogram 390. A second prescriptive fitting 344 may be generated based on the second representative audiogram 392. Similarly, a third prescriptive fitting 346 may be generated based on the third representative audiogram 394. One or more of the prescriptive fittings 342, 344, 346 may be programmed or downloaded to a memory component within the hearing aid device 340.

Figure 4:
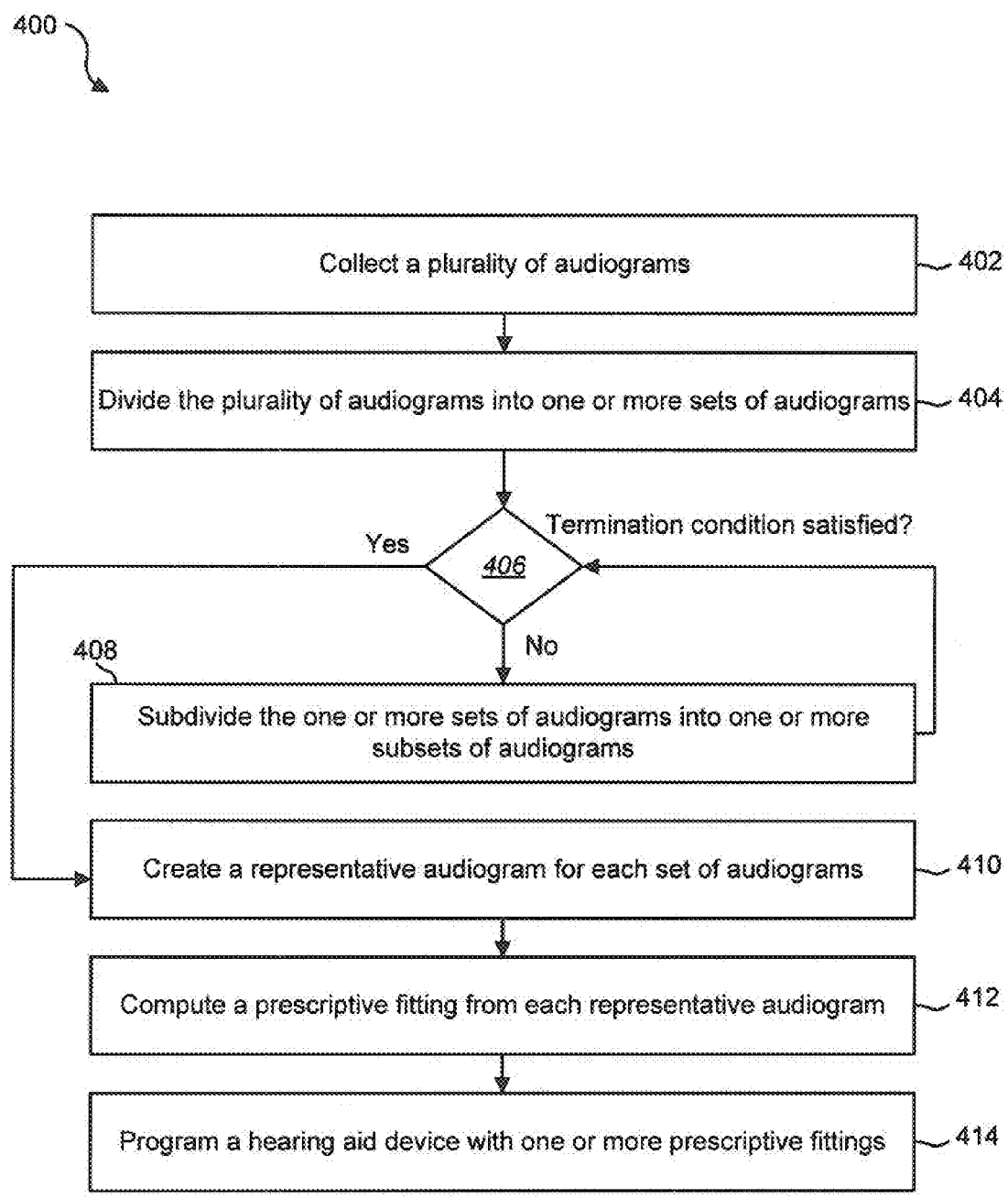
FIG. 4 is a flow diagram illustrating one embodiment of a method for obtaining prescriptive fitting targets for a hearing aid device.

FIG. 4 is a flow diagram illustrating one embodiment of a method for obtaining prescriptive fitting targets for a hearing aid device. In one configuration, a plurality of audiograms may be collected 402. The plurality of audiograms may be divided 404 into one or more sets of audiograms. A determination 406 may be made as to whether a termination condition is satisfied after the plurality of audiograms are divided 404 into one or more sets of audiograms. If it is determined that the termination condition is not satisfied, the one or more sets of audiograms may be further subdivided 408 into one or more subsets of audiograms. The determination 406 may then be made as to whether the termination condition is satisfied. If it is determined 406 that the termination condition is still not satisfied, the method 400 may continue by further subdividing 408 subsets of audiograms into one or more subsets of audiograms until the termination condition is satisfied.

If, however, it is determined 406 that the termination condition is satisfied, a representative audiogram for each set (or subset) of audiograms may be created 410. In one embodiment, a prescriptive fitting may be computed 412 from each representative audiogram. A hearing aid device may then be programmed 414 with one or more prescriptive fittings obtained from the representative audiograms.

Figure 5:
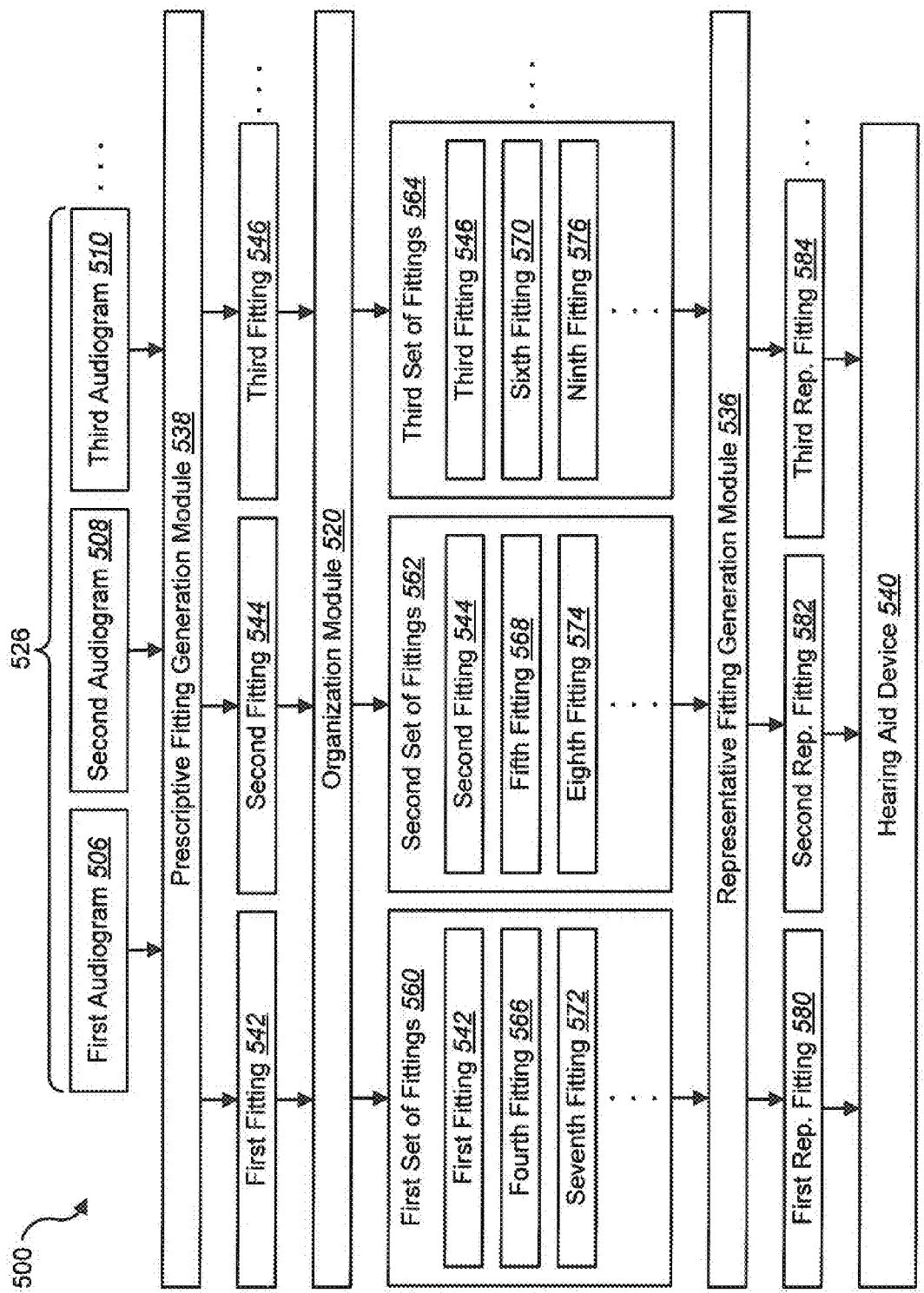
FIG. 5 is a block diagram illustrating one embodiment of modules to generate one or more representative prescriptive fittings for a hearing aid device.

FIG. 5 is a block diagram illustrating another embodiment of modules to generate one or more representative prescriptive fittings for a hearing aid device 540. In one configuration, a plurality of audiograms 526 may be analyzed by a prescriptive fitting generation module 538. For example, a first audiogram 506, a second audiogram 508, and a third audiogram 510 may be analyzed by the prescriptive fitting generation module 538. In one embodiment, the generation module 538 may generate a prescriptive fitting from each audiogram within the plurality of audiograms 526. For example, the generation module 538 may generate a first prescriptive fitting 542, a second prescriptive fitting 544, and a third prescriptive fitting 546 based on the first audiogram 506, the second audiogram 508, and the third audiogram 510, respectively.

In one example, each of the prescriptive fittings 542, 544, 546 may be provided to an organization module 520. In one embodiment, the organization module 520 may divide each fitting into one or more sets of fittings 560, 562, 564. For example, the organization module 520 may create a first set of fittings 560 that includes the first prescriptive fitting 542, a fourth prescriptive fitting 566, and a seventh prescriptive fitting 572. In addition, the organization module 520 may create a second set of fittings 562 that may include a second fitting 544, a fifth prescriptive fitting 568, and an eighth prescriptive fitting 574. Similarly, a third set of fittings 564 may be created by the organization module 520. In one embodiment, the third set of fittings 564 may include the third prescriptive fitting 546, a sixth prescriptive fitting 570, and a ninth prescriptive fitting 576. The sets of fittings 560, 562, 564 may be further subdivided into further subsets until a termination condition is satisfied. For clarity and ease of understanding, however, additional subsets of fittings are not illustrated.

In one configuration, each of the sets of fittings 560, 562, 564 may be analyzed by a representative fitting generation module 536. In one example, the generation module 536 may generate a representative fitting 580, 582, 584 that is representative of each set of fittings 560, 562, 564. In other words, the generation module 536 may generate a first representative fitting 580 that is representative of the first set of fittings 560. In addition, a second representative fitting 582 may be generated that is representative of the second set of fittings 562. Similarly, a third representative fitting 584 may be generated that is representative of the third set of fittings 564. The representative fittings 580, 582, 584 may be generated by taking the mean of each set of fittings 560, 562, 564. For example, the first representative fitting 580 may be generated by taking the overall mean of the fittings within the first set of fittings 560. In one configuration, the hearing aid device 540 may be programmed with one or more of the representative fittings 580, 582, 584.

Figure 6:
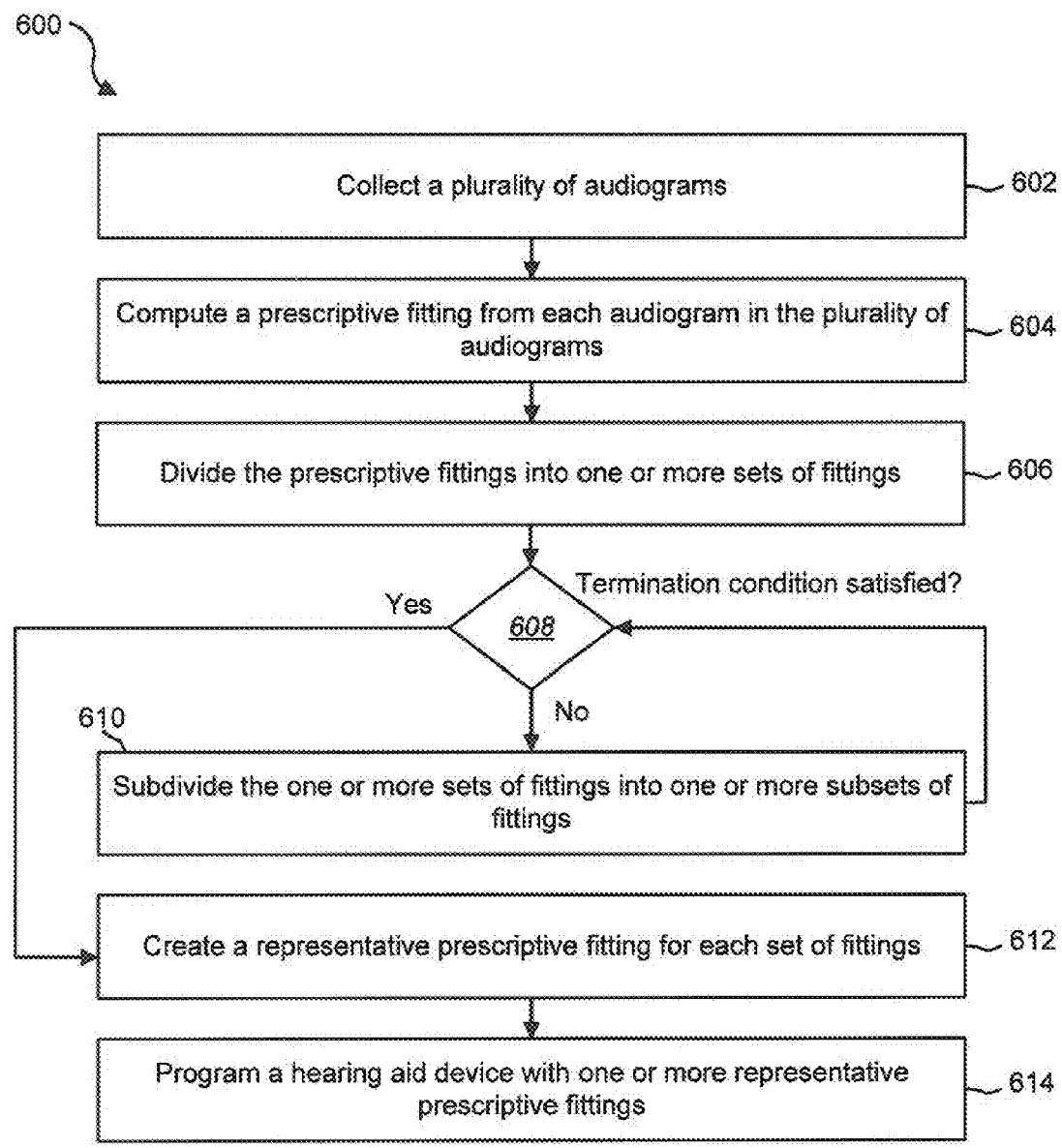
FIG. 6 is a flow diagram illustrating one embodiment of a method for obtaining representative prescriptive fittings for a hearing aid device.

FIG. 6 is a flow diagram illustrating another embodiment of a method for obtaining representative prescriptive fittings for a hearing aid device. In one embodiment, a plurality of audiograms may be collected 602. A prescriptive fitting may be computed 604 from each audiogram in the plurality of audiograms. In one embodiment, the prescriptive fittings may be divided 606 into one or more sets of fittings. A determination 608 may be made as to whether a termination condition is satisfied. If it is determined 608 that the termination condition is not satisfied, the one or more sets of fittings may be further subdivided 610 into one or more subsets of fittings. The determination 608 may then be made as to whether the termination condition is satisfied. If it is still determined that the termination condition has not been satisfied, the method 600 may continue to further subdivide 610 one or more sets (or subsets) of fittings into one or more subsets until the termination condition has been satisfied.

If, however, it is determined 608 that the termination condition has been satisfied, a representative prescriptive fitting may be created 612 for each set (or subset) of fittings. In one configuration, the hearing aid device may be programmed 614 with one or more representative prescriptive fittings.

In one embodiment, the method 400 described in FIG. 4 and the method 600 described in FIG. 6 may be combined. For example, a plurality of audiograms may be collected 402, 602. The plurality of audiograms may be divided 404 into one or more sets of audiograms. A determination 406 may be made as to whether a termination condition is satisfied after the plurality of audiograms are divided 404 into one or more sets of audiograms. If it is determined that the termination condition is not satisfied, the one or more sets of audiograms may be further subdivided 408 into one or more subsets of audiograms. The determination 406 may then be made as to whether the termination condition is satisfied. If it is determined 406 that the termination condition is still not satisfied, the method 400 may continue by further subdividing 408 subsets of audiograms into one or more subsets of audiograms until the termination condition is satisfied.

If, however, it is determined 406 that the termination condition is satisfied, a representative audiogram for each set (or subset) of audiograms may be created 410. In one embodiment, a prescriptive fitting may be computed 412 from each representative audiogram. The prescriptive fittings may be divided 606 into one or more sets of fittings. A determination 608 may be made as to whether a termination condition is satisfied. If it is determined 608 that the termination condition is not satisfied, the one or more sets of fittings may be further subdivided 610 into one or more subsets of fittings. The determination 608 may then be made as to whether the termination condition is satisfied. If it is still determined that the termination condition has not been satisfied, the method 600 may continue to further subdivide 610 one or more sets (or subsets) of fittings into one or more subsets until the termination condition has been satisfied.

If, however, it is determined 608 that the termination condition has been satisfied, a representative prescriptive fitting may be created 612 for each set (or subset) of fittings. In one configuration, the hearing aid device may be programmed 614 with one or more representative prescriptive fittings.

Figure 7:
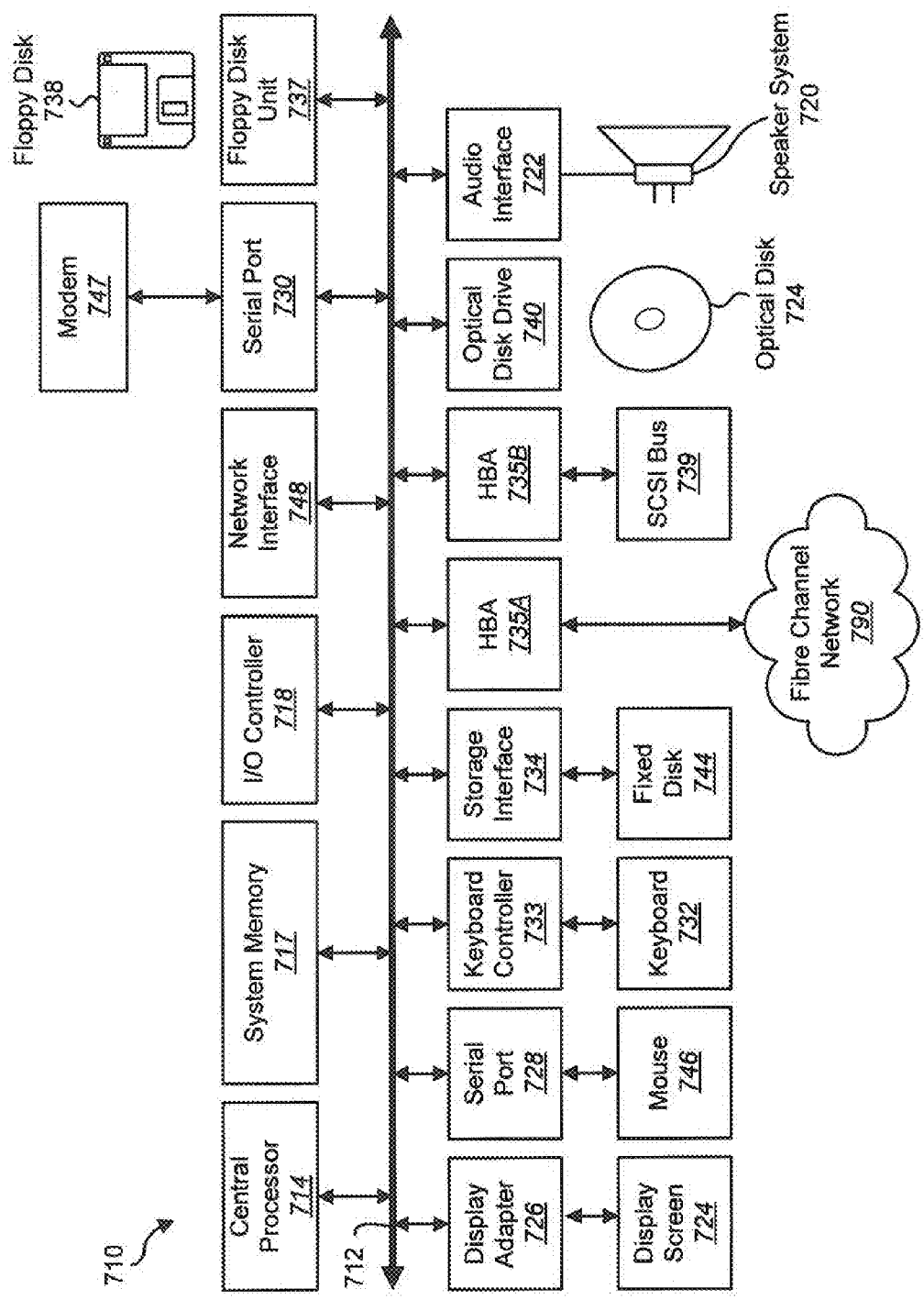
FIG. 7 depicts a block diagram of a computer system suitable for implementing the present systems and methods.

FIG. 7 depicts a block diagram of a computer system 710 suitable for implementing the present systems and methods. Computer system 710 includes a bus 712 which interconnects major subsystems of computer system 710, such as a central processor 714, a system memory 717 (typically RAM, but which may also include ROM, flash RAM, or the like), an input/output controller 718, an external audio device, such as a speaker system 720 via an audio output interface 722, an external device, such as a display screen 724 via display adapter 726, serial ports 728 and 730, a keyboard 732 (interfaced with a keyboard controller 733), a storage interface 734, a floppy disk drive 737 operative to receive a floppy disk 738, a host bus adapter (HBA) interface card 735A operative to connect with a Fibre Channel network 790, a host bus adapter (HBA) interface card 735B operative to connect to a SCSI bus 739, and an optical disk drive 740 operative to receive an optical disk 742. Also included are a mouse 746 (or other point-and-click device, coupled to bus 712 via serial port 728), a modem 747 (coupled to bus 712 via serial port 730), and a network interface 748 (coupled directly to bus 712).

Bus 712 allows data communication between central processor 714 and system memory 717, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. For example, the collection module 118, the filter 119, the organization module 120, the representative generation module 122, and the prescriptive fitting generation module 124 to implement the present systems and methods may be stored within the system memory 717. Applications resident with computer system 710 are generally stored on and accessed via a computer readable medium, such as a hard disk drive (e.g., fixed disk 744), an optical drive (e.g., optical drive 740), a floppy disk unit 737, or other storage medium. Additionally, applications can be in the form of electronic signals modulated in accordance with the application and data communication technology when accessed via network modem 747 or interface 748.

Storage interface 734, as with the other storage interfaces of computer system 710, can connect to a standard computer readable medium for storage and/or retrieval of information, such as a fixed disk drive 744. Fixed disk drive 744 may be a part of computer system 710 or may be separate and accessed through other interface systems. Modem 747 may provide a direct connection to a remote server via a telephone link or to the Internet via an internet service provider (ISP). Network interface 748 may provide a direct connection to a remote server via a direct network link to the Internet via a POP (point of presence). Network interface 748 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 7 need not be present to practice the present disclosure. The devices and subsystems can be interconnected in different ways from that shown in FIG. 7. The operation of a computer system such as that shown in FIG. 7 is readily known in the art and is not discussed in detail in this application. Code to implement the present disclosure can be stored in computer-readable storage media such as one or more of system memory 717, fixed disk 744, optical disk 742, or floppy disk 738. The operating system provided on computer system 710 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present disclosure may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A computer-implemented method for programming a hearing aid device, the method comprising:
    collecting a plurality of audiograms from a plurality of individuals, an audiogram being a collection of hearing thresholds at various frequencies for a particular individual from said plurality of individuals;
    dividing the plurality of audiograms from the plurality of individuals into one or more sets of audiograms;
    creating by a processing device a representative audiogram for each set of said one or more sets of audiograms, the representative audiogram representing multiple individuals, the representative audiogram calculated as an overall mean of audiograms in the set of said one or more sets of audiograms;
    computing a hearing enhancement fitting based on the representative audiogram; and
    programming a hearing aid device with one or more hearing enhancement fittings computed based on the representative audiogram.

2. The method of claim 1, further comprising
    subdividing the one or more sets of audiograms into one or more subsets until a termination condition is satisfied.

3. The method of claim 1, further comprising filtering one or more audiograms from the plurality of audiograms.

4. The method of claim 3, further comprising
    filtering the one or more audiograms from the plurality of audiograms that exceed a specified fitting range for the hearing aid device.

5. The method of claim 1, further comprising
    determining a mean hearing threshold at each measured frequency of each audiogram within the plurality of audiograms.

6. The method of claim 5, further comprising
    creating prototype audiograms from the mean hearing threshold.

7. The method of claim 6, further comprising
    associating each prototype audiogram with a set of audiograms.

8. The method of claim 7, further comprising
    placing an audiogram in the set of audiograms if the audiogram is similar to the prototype audiogram associated with the set.

9. The method according to claim 1, wherein each hearing enhancement fitting of said one or more of hearing enhancement fittings is selectable by a wearer of the hearing aid device.

10. A computing device configured to obtain hearing enhancement fittings and program a hearing aid device, comprising:
    a processor;
    memory in electronic communication with the processor;
    a collection module configured to collect a plurality of audiograms from a plurality of individuals, an audiogram being a collection of hearing thresholds at various frequencies for a particular individual from said plurality of individuals;
    an organization module configured to divide the plurality of audiograms from the plurality of individuals into one or more sets of audiograms;
    a representative generation module configured to create a representative audiogram for each set of said one or more sets of audiograms, the representative audiogram representing multiple individuals, the representative audiogram calculated as an overall mean of audiograms in the set of said one or more sets of audiograms; and
    a fitting generation module configured to compute a hearing enhancement fitting based on the representative audiogram, and program a hearing aid device with one or more hearing enhancement fittings computed based on the representative audiogram.

11. The computing device of claim 10, wherein
    the organization module is further configured to subdivide the one or more sets of audiograms into one or more subsets until a termination condition is satisfied.

12. The computing device of claim 10, further comprising
    a filter configured to filter one or more audiograms from the plurality of audiograms.

13. The computing device of claim 12, wherein
    the filter is further configured to filter one or more audiograms from the plurality of audiograms that exceed a specified fitting range for the hearing aid device.

14. The computing device of claim 10, wherein
    the organization module is further configured to determine a mean hearing threshold at each measured frequency of each audiogram within the plurality of audiograms.

15. The computing device of claim 14, wherein
    the organization module is further configured to create prototype audiograms from the mean hearing threshold.

16. The computing device of claim 15, wherein
    the organization module is further configured to associate each prototype audiogram with a set of audiograms.

17. The computing device of claim 16, wherein
    the organization module is further configured to place an audiogram in the set of audiograms if the audiogram is similar to the prototype audiogram associated with the set.

18. The computing device according to claim 10, wherein each hearing enhancement fitting of said one or more of hearing enhancement fittings is selectable by a wearer of the hearing aid device.

19. A computer-readable non-transitory recording medium encoded with instructions, wherein the instructions, when executed on a computer cause the computer to perform a method, the method comprising:
    collecting a plurality of audiograms from a plurality of individuals, an audiogram being a collection of hearing thresholds at various frequencies for a particular individual from said plurality of individuals;
    dividing the plurality of audiograms from the plurality of individuals into one or more sets of audiograms;
    creating a representative audiogram for each set of said one or more sets of audiograms, the representative audiogram representing multiple individuals, the representative audiogram calculated as an overall mean of audiograms in the set of said one or more sets of audiograms;

computing a hearing enhancement fitting based on the representative audiogram; and programming a hearing aid device with one or more hearing enhancement fittings computed based on the representative audiogram.

20. The computer-readable non-transitory recording medium according to claim 19, wherein each hearing enhancement fitting of said one or more of hearing enhancement fittings is selectable by a wearer of the hearing aid device.

\* \* \* \* \*